US011278260B1

(12) United States Patent
Putha et al.

(10) Patent No.: US 11,278,260 B1
(45) Date of Patent: Mar. 22, 2022

(54) ACQUIRING ULTRASOUND IMAGE (71) Applicant: Qure.ai Technologies Private Limited, Mumbai (IN)

(72) Inventors: Preetham Putha, Guntur (IN); Manoj Tadepalli, Gudivada (IN); Prashant Warier, Mumbai (IN); Pooja Rao, Pune (IN); Rohan Sahu, Bengaluru (IN)

(73) Assignee: QURE.AI TECHNOLOGIES PRIVATE LIMITED, Mumbai (IN)

( * ) Notice: Subject to any disclaimer, the term of this patent is extended or adjusted under 35 U.S.C. 154(b) by 0 days.

(21) Appl. No.: 17/411,285

(22) Filed: Aug. 25, 2021

(30) Foreign Application Priority Data

Jul. 9, 2021 (IN) .............................. 202121030904

(51) Int. Cl.
*A61B 5/00* (2006.01)
*A61B 8/00* (2006.01)
*A61B 8/08* (2006.01)
*A61B 90/00* (2016.01)
*G01S 15/89* (2006.01)
*G06T 19/00* (2011.01)
*G16H 50/20* (2018.01)
*G06T 7/00* (2017.01)

(52) U.S. Cl.
CPC .............. *A61B 8/466* (2013.01); *A61B 8/483* (2013.01); *A61B 8/5207* (2013.01); *A61B 90/36* (2016.02); *G01S 15/8993* (2013.01); *G06T 7/0012* (2013.01); *G06T 19/006* (2013.01); *G16H 50/20* (2018.01); *A61B 2090/365* (2016.02); *A61B 2090/367* (2016.02); *G06T 2207/10136* (2013.01)

(58) Field of Classification Search
CPC combination set(s) only.
See application file for complete search history.

(56) References Cited

U.S. PATENT DOCUMENTS

| 10,610,203 | B2 | 4/2020 | Liang et al. |
| 10,702,242 | B2 | 7/2020 | de Jonge et al. |
| 2015/0112182 | A1* | 4/2015 | Sharma ................ A61B 5/7264 600/408 |
| 2016/0007956 | A1 | 1/2016 | Mauldin, Jr. et al. |

(Continued)

FOREIGN PATENT DOCUMENTS

WO 2020131517 A1 6/2020

*Primary Examiner* — Joel F Brutus
(74) *Attorney, Agent, or Firm* — Shumaker, Loop & Kendrick, LLP (57) ABSTRACT A method and a system for acquiring a 3D ultrasound image. The method includes receiving a request to capture a plurality of ultrasound image for a medical test corresponding to a medical condition. The method further includes determining a body part corresponding to the medical test. Further, the method includes identifying an imaging site particular to the medical test. Furthermore, the method includes providing a navigational guidance to the user in real time for positioning a handheld ultrasound device. Subsequently, the user is assisted to capture the plurality of ultrasound image of the imaging site in real time using deep learning. Further, the plurality of ultrasound images of the imaging site is captured. Finally, the method includes converting the plurality of ultrasound image to a 3-Dimensional (3D) ultrasound image in real time.

13 Claims, 6 Drawing Sheets

(56) References Cited

U.S. PATENT DOCUMENTS

| | | |
|---|---|---|
| 2016/0374644 A1 | 12/2016 | Mauldin, Jr. et al. |
| 2018/0055485 A1* | 3/2018 | Lalena ................. A61B 8/0866 |
| 2019/0026956 A1* | 1/2019 | Gausebeck ............. G06T 19/20 |
| 2020/0268349 A1* | 8/2020 | Buras ..................... A61B 90/36 |
| 2021/0077062 A1 | 3/2021 | Schadewaldt et al. |

* cited by examiner

ACQUIRING ULTRASOUND IMAGE

CROSS REFERENCE TO RELATED APPLICATIONS

The present application claims priority from the Indian patent application numbered 202121030904 filed on Jul. 9, 2021 in India.

TECHNICAL FIELD

The present subject matter described herein, in general, relates to acquiring an ultrasound image.

BACKGROUND

In general practice, medical imaging techniques have always been crucial for diagnosis and monitoring of medical conditions. Such diagnostic techniques are known to necessarily require highly skilled medical professionals, radiologists, obstetricians, and gynaecologists. Further, conventional instruments used for the diagnostic techniques require appropriate set up, assembling, and operational skills to be worked upon. It is well known that obtaining an ultrasound report requires at least skilled medical professionals, a lab facility, or a diagnostic centre. Further, an interpretation of the ultrasound report requires skilled professionals such as radiologists and doctors as well. Typically, non-clinicians such as nurses, physiotherapists, heath care providers and patients are not trained and equipped to perform the conventional diagnostic techniques. For the above-mentioned reasons, obtaining and interpreting the ultrasound report may become time consuming and challenging.

SUMMARY

Before the present system(s) and method(s), are described, it is to be understood that this application is not limited to the particular system(s), and methodologies described, as there can be multiple possible embodiments which are not expressly illustrated in the present disclosure. It is also to be understood that the terminology used in the description is for the purpose of describing the particular implementations or versions or embodiments only and is not intended to limit the scope of the present application. This summary is provided to introduce aspects related to a system and a method for acquiring a 3D ultrasound image. This summary is not intended to identify essential features of the claimed subject matter nor is it intended for use in determining or limiting the scope of the claimed subject matter.

In one embodiment, a method for acquiring a 3D ultrasound image is disclosed. Initially, a request to capture a plurality of ultrasound images for a medical test corresponding to a medical condition may be received. It may be understood that the request may be received from a user on a wireless display device. Further, a body part corresponding to the medical test may be determined. It may be noted that the body part may be determined based upon a historical knowledge base in order to capture the plurality of ultrasound images relevant for the medical test. Subsequently, an imaging site particular to the medical test may be identified. It may be noted that the imaging site may be identified from the historical knowledge base of the medical test and the imaging site may be a portion of the body part. Further, a navigational guidance may be provided in real time for positioning a handheld ultrasound device at the imaging site. It may be noted that the navigational guidance may be based on deep learning and the navigational guidance may be provided in natural language. Furthermore, the user may be assisted to capture the plurality of ultrasound images of the imaging site in real time using deep learning. It may be understood that the assistance may comprise a real time feedback on at least an image quality, automated measurements, coverage calculations, angular calculations, and characterizations specific to the ultrasound images of the medical condition. Subsequently, the plurality of ultrasound images of the imaging site may be captured when the handheld ultrasound device may be positioned within a permissible radius of operation. It may be understood that the plurality of ultrasound images may be captured based on the assistance and the plurality of ultrasound images may be a 2-Dimensional (2D) image. Finally, the plurality of ultrasound images may be converted to a 3-Dimensional (3D) ultrasound image in real time. It may be noted that the plurality of ultrasound images may be stitched together to form the 3D ultrasound image using an Artificial Intelligence (AI) enabled image model. In one aspect, the aforementioned method for acquiring the 3D ultrasound image may be performed by a processor using programmed instructions stored in a memory.

In another embodiment, a non-transitory computer-readable medium embodying a program executable in a computing device for acquiring a 3D ultrasound image is disclosed. The program may comprise a program code for receiving a request to capture a plurality of ultrasound image for a medical test corresponding to a medical condition. It may be noted that the request may be understood that the request may be received from a user on a wireless display device. Further, the program may comprise a program code for determining a body part corresponding to the medical test. It may be noted that the body part may be determined based upon a historical knowledge base in order to capture the plurality of ultrasound images relevant for the medical test. Subsequently, the program may comprise a program code for identifying an imaging site particular to the medical test. It may be noted that the imaging site may be identified from the historical knowledge base of the medical test and the imaging site may be a portion of the body part. Further, the program may comprise a program code for providing a navigational guidance in real time for positioning a handheld ultrasound device at the imaging site. It may be noted that the navigational guidance may be based on deep learning and the navigational guidance may be provided in natural language. Furthermore, the program may comprise a program code for assisting the user to capture the plurality of ultrasound images of the imaging site in real time using deep learning. It may be understood that the assistance may comprise a real time feedback on at least an image quality, automated measurements, coverage calculations, angular calculations, and characterizations specific to the ultrasound images of the medical condition. Subsequently, the program may comprise a program code for capturing the plurality of ultrasound images of the imaging site when the handheld ultrasound device may be positioned within a permissible radius of operation. It may be understood that the plurality of ultrasound images may be captured based on the assistance and the plurality of ultrasound images may be a 2-Dimensional (2D) image. Finally, the program may comprise a program code for converting the plurality of ultrasound images to a 3-Dimensional (3D) ultrasound image in real time. It may be noted that the plurality of ultrasound images may be stitched together to form the 3D ultrasound image using an Artificial Intelligence (AI) enabled image model.

BRIEF DESCRIPTION OF THE DRAWINGS

The foregoing detailed description of embodiments is better understood when read in conjunction with the appended drawings. For the purpose of illustrating of the present subject matter, an example of a construction of the present subject matter is provided as figures, however, the invention is not limited to the specific method and system for acquiring a 3D ultrasound image, disclosed in the document and the figures.

The present subject matter is described in detail with reference to the accompanying figures. In the figures, the left-most digit(s) of a reference number identifies the figure in which the reference number first appears. The same numbers are used throughout the drawings to refer to various features of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "identifying," "determining," "receiving," "providing," "assisting," "capturing," "converting," and other forms thereof, are intended to be open ended in that an item or items following any one of these words is not meant to be an exhaustive listing of such item or items or meant to be limited to only the listed item or items.

It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described but is to be accorded the widest scope consistent with the principles and features described herein.

The present subject matter discloses a method and a system for acquiring a 3D ultrasound image. Generally, when a patient is unwell there is a requirement for a patient to consult a doctor and get diagnosed. The consultation may involve application of medical diagnostic techniques broadly referred as medical imaging techniques. The medical imaging techniques comprise various invasive and non-invasive techniques and processes to diagnose the patient's body parts for abnormalities.

Further, the medical imaging techniques comprise an ultrasound imaging, doppler ultrasound measurements, Magnetic Resonance Imaging (MRI), X-rays, fluoroscopic imaging techniques and the like. It may be understood that the various techniques assist in diagnosis as well as treatment of medical conditions. However, the above-mentioned imaging techniques necessarily require trained medical professionals for executing as well as interpreting the results of medical tests.

It may be understood that consulting a doctor, seeking an appointment for conventional ultrasound, undergoing the ultrasound, procuring the ultrasound reports, and then getting the ultrasound reports interpreted by doctors, radiologists and the like may become a time-consuming process. Also, sometimes the ultrasound reports may be required to only monitor a status of a known medical condition which may not require human intervention.

The present invention aims to simplify the conventional ultrasound technique by enabling non-clinical technicians, nurses, and patients to perform the ultrasound with help of Artificial Intelligence (AI). The present invention utilizes historical data of a set of patients for various medical conditions to train the AI enabled models. Therefore, the present invention makes it possible for a layman to view, capture and interpret a 3D ultrasound using a handheld ultrasound device and a wireless display device.

While aspects of described system and method for acquiring a 3D ultrasound image executed on a software may be implemented in any number of different computing systems, environments, and/or configurations, the embodiments are described in the context of the following exemplary system.

Figure 1:
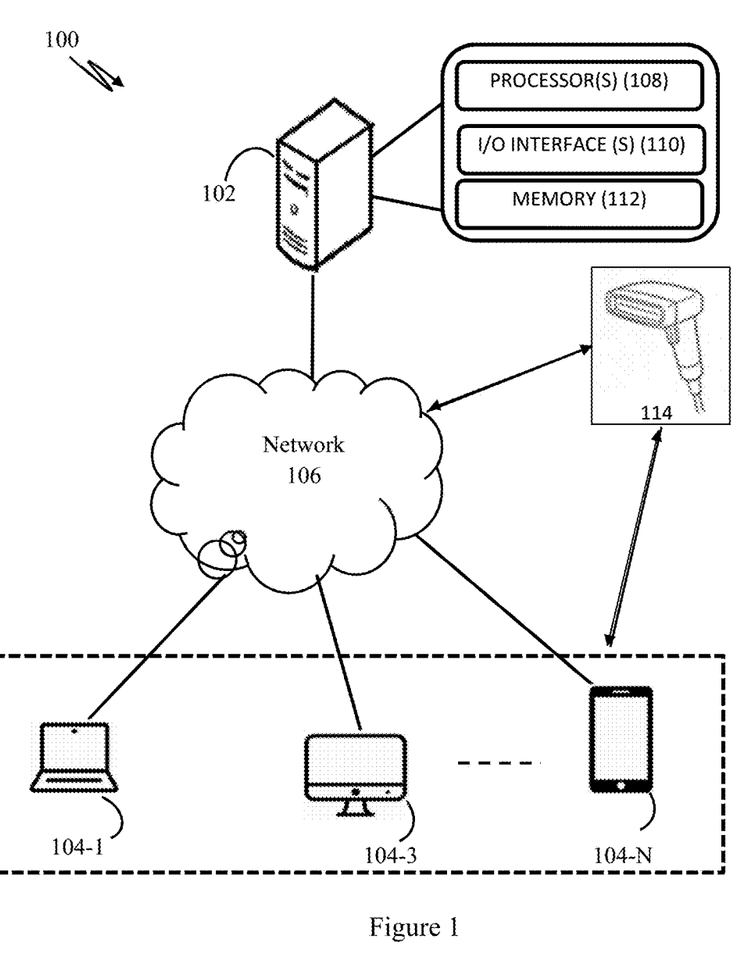
FIG. 1 illustrates a network implementation of a system for acquiring a 3D ultrasound image, in accordance with an embodiment of the present subject matter.

Referring now to FIG. 1, a network implementation 100 of a system 102 for acquiring a 3-Dimensional (3D) ultrasound image is disclosed. Initially, the system 102 may allow a user to register on a native application of a software on a wireless display device 104. The user may also connect the wireless display device to a handheld ultrasound device 114. Further, a request to capture a plurality of ultrasound images for a medical test corresponding to a medical condition may be received by the system 102.

In an example, the software may be installed on the wireless display device also referred to as a user device 104-1. It may be noted that the one or more users may access the system 102 through one or more user devices 104-2, 104-3 . . . 104-N, collectively referred to as user devices 104, hereinafter, or applications residing on the user devices 104.

In one example, the users may include, but not be limited to, patients, doctors, medical practitioners, nurses, non-clinicians, clinical researchers, and any other health service providers. The system 102 may receive the request for capturing the plurality of ultrasound images for the medical test corresponding to the medical condition from one or more user devices 104. Further, the system 102 may also receive a feedback from the user using the user devices 104.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-2 . . . 104-N.

In one implementation, the system 102 may comprise a cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown).

The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random-access memory (SRAM) and dynamic random access memory (DRAM), and/or non-volatile memory, such as read only memory (ROM), erasable programmable ROM, flash memories, hard disks, Solid State Disks (SSD), optical disks, and magnetic tapes.

The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for acquiring a 3D ultrasound image. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for acquiring the 3D ultrasound image in real time without intervention of any skilled medical professional, and a diagnostic laboratory set up. The user may be guided automatically for acquiring the 3D ultrasound image using the handheld ultrasound device 114. In one embodiment of the present invention, the system 102 may receive a request to capture a plurality of ultrasound images for a medical test corresponding to a medical condition.

The medical test may also be referred to as a diagnostic test with a specific procedure to monitor and diagnose the medical condition. The medical condition may be understood as a disease condition which is detected using one or more medical tests. In one case, a single medical test may be required to diagnose multiple medical conditions. In another case, a single medical condition may require multiple medical tests for diagnosis and treatment. In one example, the medical test corresponding to the medical condition may be known to the user. In another example, the medical test may be suggested by the medical professionals.

Further, the user may request to the system 102 to capture a plurality of ultrasound images for the medical test corresponding to the medical condition on the wireless display device 104. It may be understood that the wireless display device 104 is connected to the handheld ultrasound device 114. The wireless display device 104 may have the native application of the system 102 installed and is connected to the network 106. In one example, the wireless display device 104 may be a mobile. In another example, the wireless display device may be a tablet or a laptop.

Upon receiving the request, the system 102 may determine a body part corresponding to the medical test. The body part may be determined based on a historical knowledge base. In one example, the historical knowledge base may be understood as a repository storing medical data of a set of users associated to various medical conditions. The historical knowledge base may be updated in real time upon receiving the feedback from the user. In one example, the medical condition may be a carotid stenosis and the body part determined by the system 102 may be a carotid artery. In another example, the medical condition may be a cardiovascular risk and the body part determined by the system 102 is a carotid artery for determining a risk of myocardial infarction and other cardiovascular diseases.

Subsequent to determining the body part corresponding to the medical test, the system 102 may identify an imaging site particular to the medical test. The imaging may be a portion of the body part and is identified from the historical knowledge base. It may be understood that the body part determined by the system 102 may stretch across a large area and the imaging site is the portion of the body part which is easily accessible and proved to be relevant for ultrasound. In one example, the medical condition may be abdominal pain and the imaging site for the ultrasound may be a gall bladder.

Further, the system 102 may provide a navigational guidance in real time for positioning the handheld ultrasound device 114 at the imaging site. The navigational guidance may be provided in natural language. The navigational guidance may be based on deep learning. The deep learning uses the historical knowledge base comprising the medical data from the set of users. The medical data may comprise raw data, medical history, ultrasound reports and analysis reports for various medical conditions. The medical data may be stored in a predefined input format for training one or more of the AI-enabled models. In one aspect, the AI-enabled models may be continuously learning from the feedback received from the set of users. Therefore, the deep learning may form the basis of the navigational guidance provided by the system 102 in real time.

In one embodiment, a smart visualization device 115 may be used by a user instead of the wireless display device 104. The smart visualization device 115 may be connected to the system 102 through the network 106. Further, the smart visualization device 115 may allow the user to visualize the navigational guidance and the assistance provided by the system 102 in real time. Furthermore, the smart visualization device 115 may also send a visual data as an input to the system 102 in real time. The inputs may be provided to the system 102 in a virtual reality and an augmented reality as well. In one example, the smart visualization device 115 may be a smart contact lens. The smart contact lens may comprise a camera component, a contact lens, a control circuit, and a visual sensor. In another example, the smart visualization device 115 may be a smart glass. The smart glass may be understood to be a wearable glass with a head gear for the user. Further, the smart glass may comprise a Central Processing Unit (CPU), a camera, a battery, a Global Positioning System (GPS), a microphone, and a speaker.

Further, the navigational guidance may be a set of instructions displayed on the wireless display device 104 for positioning the handheld ultrasound device 114. The set of instructions may be provided in a textual, a verbal, and a speech format. Example of the set of instructions provided to the user may include 'move the probe closer to the neck', 'move the probe slightly towards right, 'position the device near the skin', and the like. It may be understood that the navigational guidance is critical for acquiring the plurality of ultrasound images. The aim of navigational guidance is to make the handheld ultrasound device 114 reach the imaging site required for the medical test.

Upon providing the navigational guidance, the system 102 may assist to capture the plurality of ultrasound images of the imaging site in real time using the deep learning. It may be understood that through the deep learning the AI-enabled models may identify the appropriate image quality for accurate measurements and analysis of the plurality of ultrasound images. The assistance may comprise a real time feedback on at least an image quality, automated measurements, coverage calculations, angular calculations, and characterizations specific to the ultrasound images of the medical condition. It may be understood that the assistance is displayed in real time on the wireless display device 104. In one example, the system 102 may assist the user in real time by providing assistance to focus and operate optimally.

Examples of assistance provided to the user may include instructions to capture the plurality of ultrasound images above a predefined threshold of image quality. In one aspect, the predefined threshold may be 90%. Further, the system 102 may alert the user if the image quality of an ultrasound is below 90%. Furthermore, the system 102 may assist the user to capture another ultrasound image. In such case, the system 102 may display instructions such as 'Low Image Quality'. The system 102 may further auto focus to capture when image quality exceeds above 90%. Similarly, the system 102 may assist the user in capturing the plurality of ultrasound images based on the predefined threshold for each of the automated measurements, the coverage calculations, the angular calculations, and the characterizations specific to the medical condition.

In one embodiment, the handheld ultrasound device 114 may further be coupled to a gyroscope sensor 113. Further, the gyroscope sensor 113 may be connected to the system 102 through the network 106. The gyroscope sensor 113 may be understood as a device that may measure, monitor and transmit angular data. The angular data may comprise an angle, an angular velocity, and an orientation of the coupled device, i.e., the handheld ultrasound device 114. Further, the system 102 may receive the angular data of the handheld ultrasound device 114 from the gyroscope sensor 113. The system 102 may use the angular data to provide the navigational guidance and the assistance to the user in real time.

Further, the system 102 may capture the plurality of ultrasound images of the imaging site when the handheld ultrasound device 114 is positioned within a permissible radius of operation. The plurality of ultrasound images may be 2-Dimensional (2D) images captured based on the assistance provided by the system 102. In one example, the permissible radius may be within 15 cm from the imaging site. Further, the plurality of ultrasound images may be displayed in real time on the wireless display device. It may be understood that images above the predefined threshold is captured by the system 102. In one example, the system 102 may alert the user upon capturing the plurality of ultrasound images. The alert may correspond to displaying a notification 'Image captured' on the wireless display device 104.

Finally, the system 102 may convert the plurality of ultrasound images to a 3-Dimensional (3D) ultrasound image in real time. The plurality of ultrasound images may be stitched together to form the 3D ultrasound image using an Artificial Intelligence (AI) enabled image model. It may be understood that the AI enabled image model may arrange and convert the plurality of ultrasound images based on a set of images, associated with the set of users, stored in the historical knowledge base. The aim of converting the plurality of ultrasound images to the 3D ultrasound image is to analyse and interpret the ultrasound accurately and precisely.

Further, the 3D ultrasound image may be analyzed using the deep learning. The system 102 may identify a plurality of characteristics relating to the imaging site based on the analysis. The plurality of characteristics may be specific for the medical condition. The plurality of characteristics may comprise a set of morphological and physiological specifications of the imaging site. Further, the morphological specifications may be referred to as the structural specifications or structural properties of the imaging site.

In one example, the system 102 may identify the plurality of characteristics for the carotid artery that are pre-defined for the carotid stenosis. It may be understood that the historical knowledge base may comprise details of the symptoms involved in all possible medical conditions and the plurality of characteristics may be related to the symptoms visually observable. Therefore, the plurality of characteristics for the carotid stenosis may comprise an intima media thickness, a presence of plaque, a height of plaque, a density of plaque, a doppler assessment, and an area of plaque in the imaging site of the carotid artery.

It may be noted that the medical condition of carotid stenosis is known to occur due to presence of the plaque in the carotid artery leading to narrowing of the carotid intima media thickness. Further, the height of plaque, the density of plaque and the area of plaque may help in determining a severity of the carotid stenosis which in turn may predict the risk of stroke for the user.

Further to identifying the plurality of characteristics, the system 102 may compare the plurality of characteristics with a trained data model using deep learning. It may be understood that the trained data model may comprise historical data relating to the medical condition associated with a set of users. In one embodiment, the historical data may comprise predefined characteristics of the imaging site. In one example, the height of plaque may be compared with predefined height from the historical data, the density of plaque may be compared with predefined density from the historical data, and the like.

Furthermore, the system 102 may generate an analysis report for the plurality of characteristics based on the 3D ultrasound image for the medical test. The analysis report may comprise inference and further suggestions for the user. Further, the analysis report may display the results for the plurality of characteristics and characterization details. The user may be allowed to save and share a copy of the analysis report with another user. In one example, the analysis report may comprise automated measurements on the imaging site, presence, or absence of the plaque in carotid artery, prediction of mild stenosis in the right carotid artery and the like.

It may be understood that the navigational guidance, the assistance, the plurality of ultrasound images, the 3D ultrasound image and the analysis report may be displayed in real time on the wireless display device.

Figure 2:
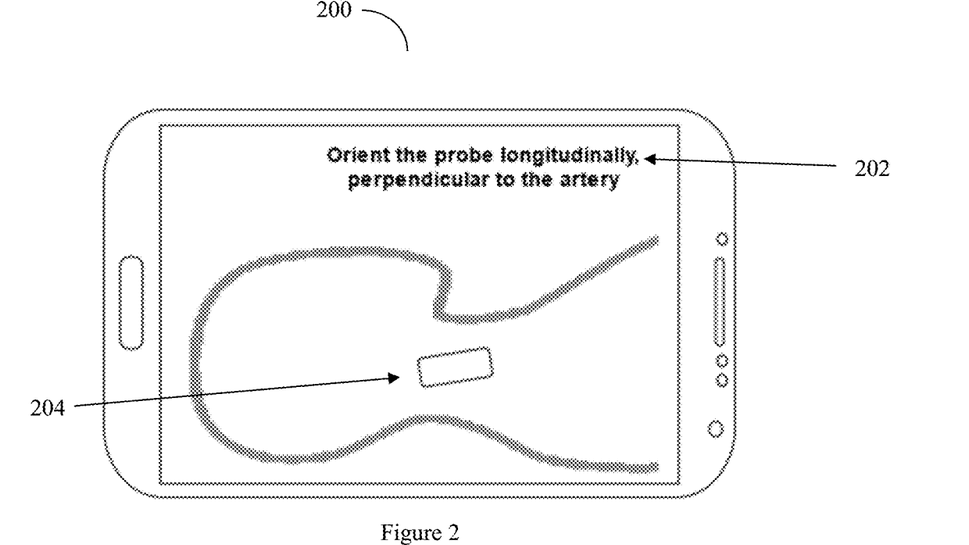
FIG. 2, FIG. 3, FIG. 4, FIG. 5, FIG. 6, FIG. 7, FIG. 8, and FIG. 9 illustrate an exemplary embodiment of the system, in accordance with an embodiment of the present subject matter.

Referring now to FIG. 2, exemplary embodiment 200 of the system 102 is disclosed in accordance with the present subject matter. In an exemplary case of a carotid artery ultrasound shall be described in following paragraphs. It may be understood that the present disclosure may not be limited to the carotid artery ultrasound technique and may be applied for various other ultrasound such as a lung ultrasound, an ultrasound for blood disorders like haemophilia to detect bleeding in joints of users, sickle cell anaemia, an ultrasound for lower limbs to detect thrombosis, an ultrasound for rheumatoid arthritis, and related auto-immune diseases, and several other medical conditions for corresponding body parts.

Referring now to the exemplary application of the carotid artery ultrasound. It may be understood that two of the carotid arteries are located on either side of the neck in humans and the carotid arteries deliver blood from the heart to the brain. In one example, a user may suffer from a medical condition such as a Transient Ischemic Attack (TIA). In another example, the user may suffer from another medical condition such as hypertension. In yet another example, the user may suffer from one or more of the medical conditions such as diabetes, high cholesterol, a carotid stenosis and a coronary heart disease.

It may be noted that the user suffering from the above-mentioned medical conditions may have an increased risk of undergoing a severe medical condition such as a stroke. Further, the stroke may be understood as a medical emergency condition in which the blood supply to the brain may be interrupted or reduced thereby resulting in death of a plurality of brain cells.

In one example, the medical test may be a carotid ultrasound of a user and the medical condition may be a carotid stenosis in accordance with the present disclosure. It may be noted that the carotid ultrasound may be a non-invasive and a painless medical test. Further, to acquire a 3D ultrasound image, the user may procure a handheld ultrasound device 114. Furthermore, the handheld ultrasound device 114 may be connected to the system 102 through a software installed on a wireless display device 104 of the user.

Further, the user may access the system 102 on a mobile device 104 to capture a plurality of ultrasound images for the carotid ultrasound medical test. Upon receiving the request, the system 102 may determine the body part as the carotid artery. It may be understood that the system 102 may determine the body part based upon a historical knowledge base. The historical knowledge base may be understood to comprise medical data pertaining to a group of users suffering from the carotid stenosis condition and the ultrasound test reports of the group of users. Therefore, the historical knowledge base may be used to determine the body part corresponding to the medical tests.

Further, the system 102 may identify an imaging site 204 particular to the carotid ultrasound medical test. In one example, the system 102 may identify the imaging site 204 as a neck region of the user. Particularly, the neck region above the right or the left carotid artery may be identified as the imaging site 204 for the user. For instance, the imaging site 204 may be the portion of neck beneath which the carotid artery may be passing through towards the brain.

Subsequently, the system 102 may provide a navigational guidance 202 in real time for positioning the handheld ultrasound device 114 at the imaging site 204. The system 102 may provide the navigational guidance 202 as "Orient the probe longitudinally, perpendicular to the artery" on the wireless display device 104 or the mobile app of the user.

It may be understood that the system 102 may continuously provide the navigational guidance from a start point where the user may hold the handheld ultrasound device 114 in his hand till an end point where the user may hold the handheld ultrasound device 114 accurately at the imaging site. In one example the user may be navigated by the system 102 from the palm to the carotid artery in the neck region.

In one example, the system 102 may continuously monitor an image quality and auto focus the handheld ultrasound device 114 after positioning at the imaging site to gain optimal level of image quality. Further, the image quality may be considerable for the system 102 to perform several automated measurements of the imaging site, to calculate coverages, angles and perform characterizations.

In one example, the system 102 may continue providing assistance until an optimal quality image of the carotid stenosis are captured. It may be noted that the assistance may be provided on the mobile app of the user. The system 102 further converts the plurality of ultrasound images from 2D to 3D. In one embodiment, the navigational guidance and the assistance may be provided by system 102 in at least a Virtual Reality (VR) and an Augmented Reality (AR) based 3-Dimensional model to the user.

Subsequently, the system 102 may analyse the 3D ultrasound image using deep learning. Further, the system 102 may identify a plurality of characteristics associated with the left carotid artery. In one example, the plurality of characteristics may comprise an intima media thickness, a presence of plaque, a height of plaque, a density of plaque, a doppler assessment, and an area of plaque in the carotid artery.

Further, the system 102 may generate an analysis report for the plurality of characteristics. In one aspect, the plurality of characteristics may be compared with a training data model. In on example, the height of plaque may be compared with predefined height from the historical data, the density of plaque may be compared with predefined density from the historical data, and the like. Upon comparing, the analysis report for the plurality of characteristics may be displayed to the user.

Figure 3:
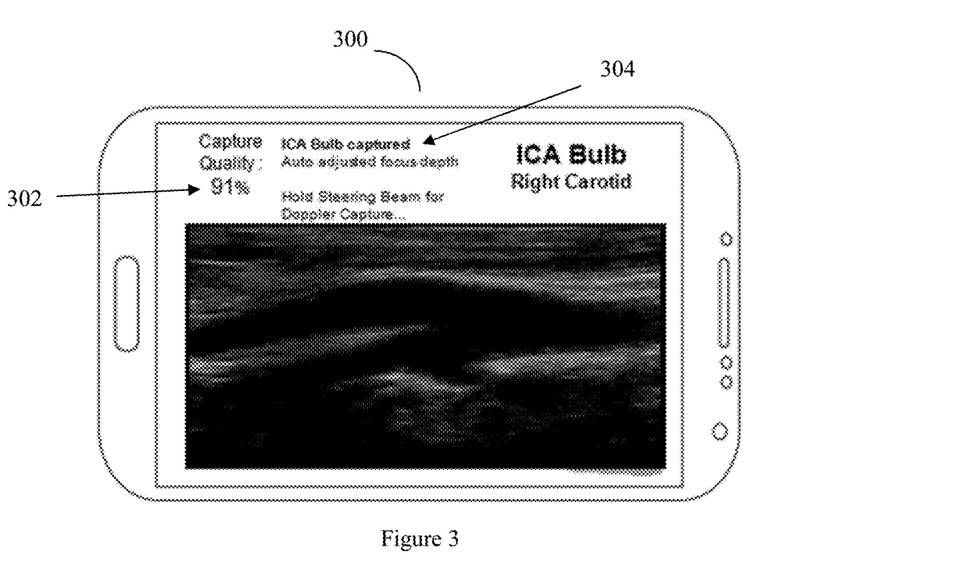

Referring now to FIG. 3, an exemplary embodiment 300 of the system 102 is illustrated in accordance with an embodiment of the present matter. It may be observed that the system 102 is assisting the user in real time by displaying the capture quality 302 as 91% in real time for the right carotid ultrasound. Further, the system 102 is also providing real time feedback 304 by displaying "ICA Bulb captured", "Auto-adjusted focus depth", and "Hold Steering Beam for Doppler capture". The assistance may be understood to help the user to capture the plurality of ultrasound images. Further the plurality of ultrasound images may be converted to a 3D ultrasound image for further analysis.

Figure 4:
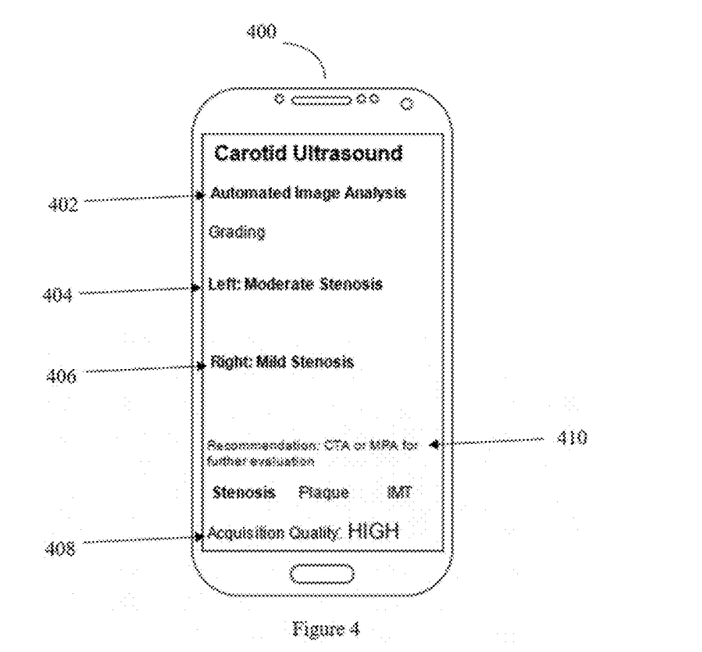

Referring now to FIG. 4, an exemplary embodiment 400 of the system 102 is illustrated in accordance with an embodiment of the present matter. It may be observed that the system 102 has performed an automated image analysis 402 of a Carotid ultrasound. Further, the system 102 may be predicting Moderate stenosis 404 condition in the left carotid artery and Mild stenosis 406 condition in the right carotid artery. The acquisition quality 408 of the acquired Carotid ultrasound has been regarded as high by the system 102. Further, the system 102 may provide an analysis report 410 recommending 'CTA or MRA for further evaluation'. The CTA may be understood as Computed Tomography Angiography and the MRA may be understood as Magnetic Resonance Angiography.

Figure 5:
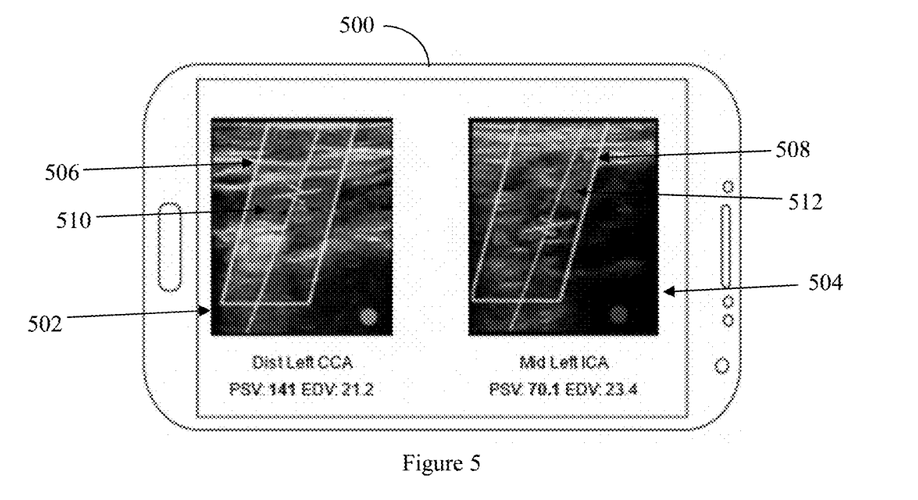

Referring now to FIG. 5, an exemplary embodiment 500 of the system 102 is illustrated in accordance with an embodiment of the present matter. It may be observed that the system 102 has automatically calculated PSV as 141 and EDV as 21.2 for the Dist Left Common Carotid Artery (CCA) 502. Further, the system 102 has calculated PSV as 70.1 and EDV as 23.4 for the Mid Left Internal Carotid Artery (ICA) 504. Furthermore, FIG. 5 also illustrates an imaging site 506 for a doppler assessment of the CCA and another imaging site 508 for the doppler assessment of the ICA. It may be understood that typically the doppler assessment may require highly skilled medical professional, such as a doctor, and a physician to identify the imaging site 506 and 508 accurately. However, the system 102 may provide the navigational guidance and the assistance to the user to carry out the doppler assessment. The doppler assessment may be understood as a crucial step in identifying and evaluating a blockage to blood flow, narrowing of a blood vessel, a presence of a tumor, a reduced blood flow, an absence of blood flow, and an increased blood flow. In the doppler assessment, a blood flow may be monitored and translated into a red color patch 510 for the CCA and another red color patch 512 for the ICA. In one example, the red color may indicate the blood flow towards the handheld ultrasound device 114. In another example, a user may similarly measure an Ankle Branchial Pressure Index (ABPI) using the system 102.

Figure 6:
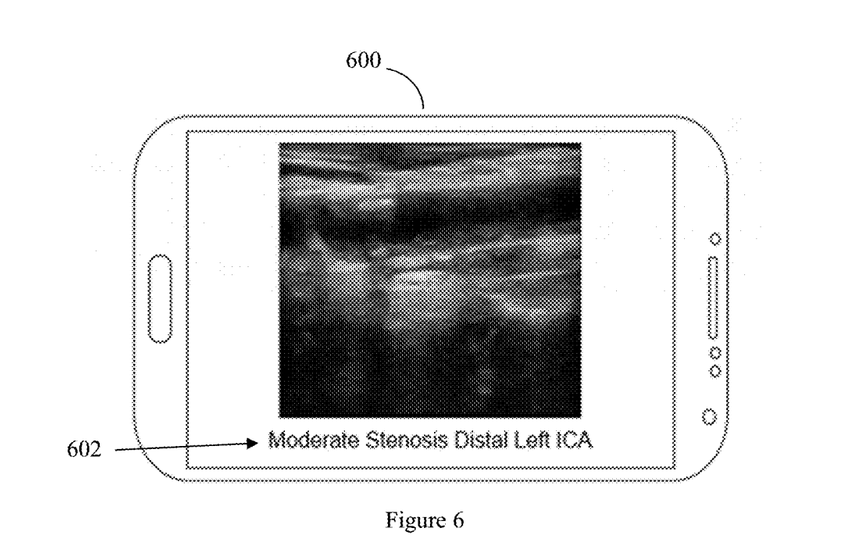

Referring now to FIG. 6, an exemplary embodiment 600 of the system 102 is illustrated in accordance with an embodiment of the present matter. It may be understood that a 3D ultrasound has been illustrated and the medical condition of "Moderate Stenosis" 602 has been identified in the Distal Left ICA 604 artery by the system 102. The ICA may be understood as the Internal Carotid Artery.

Figure 7:
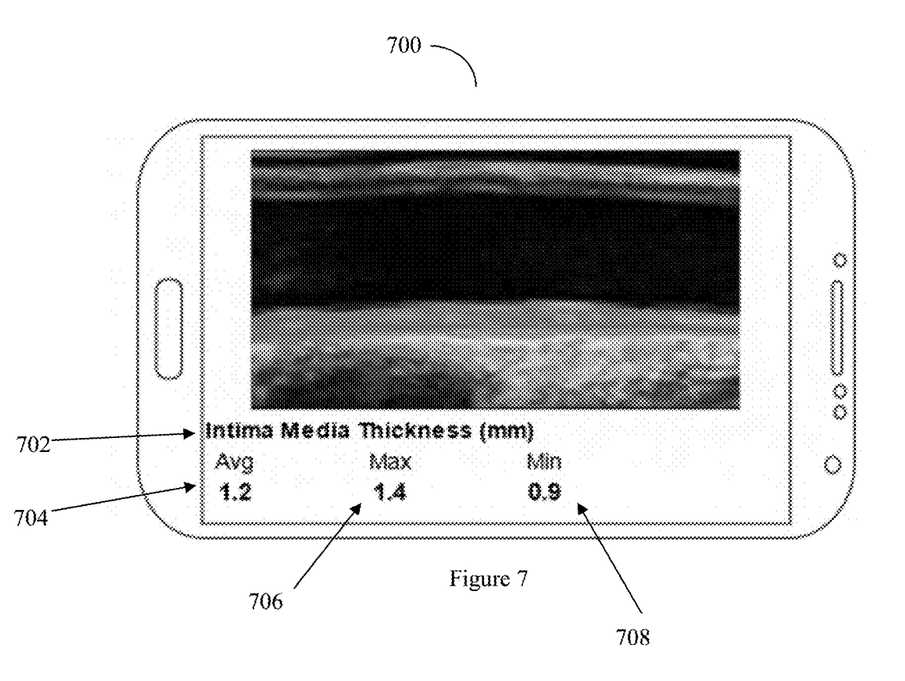

Referring now to FIG. 7, an exemplary embodiment 700 of the system 102 is illustrated in accordance with an embodiment of the present matter. It may be understood that the system 102 automatically calculated the Intima Media Thickness (IMT) 702 (in mm) of a carotid artery. The system 102 may calculate an average IMT 704 as 1.2, maximum IMT 706 as 1.4 and minimum IMT 708 as 0.9. In order to explain further, construe a 3D carotid ultrasound of a carotid artery. The IMT may be understood as a measurement of the thickness of two innermost layers of the carotid artery, namely—tunica intima and tunica media. In one example, the IMT for the carotid artery may be considered as normal if the values range between 0.6 mm to 0.7 mm. If the average value of IMT crosses 1 mm, it may be considered to be associated with higher risk for carotid stenosis, coronary heart disease and eventually stroke. Therefore, FIG. 7 illustrates a condition wherein the user should be seeking further medical opinions.

Figure 8:
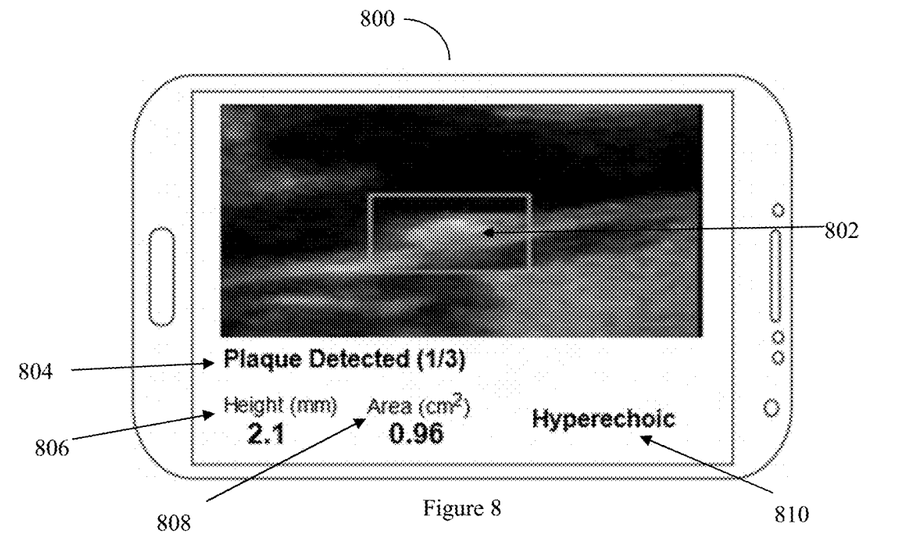

Referring now to FIG. 8, an exemplary embodiment 800 of the system 102 for the plaque detection in a carotid artery is illustrated, in accordance with an embodiment of the present subject matter. In order to illustrate further, consider a 3D carotid ultrasound depicting a presence of the plaque 802. The plaque 802 may be understood as clumps of cholesterol, calcium, fibrous tissue, and other cellular debris that may accumulate within the carotid artery.

Further, the presence of plaque 802 in the carotid artery may lead to narrowing of the carotid artery. Based upon the 3D ultrasound, presence of the plaque, height (mm) of the plaque, and area (cm$^2$) of the plaque 802 may be automatically calculated by the system 102. In FIG. 8 the system 102 displays "Plaque detected" 804 and mentions the height of plaque 806 as 2.1 mm and the area of plaque 808 as 0.96 cm$^2$. Further, the plaque may be characterized to be hyperechoic 810.

Figure 9:
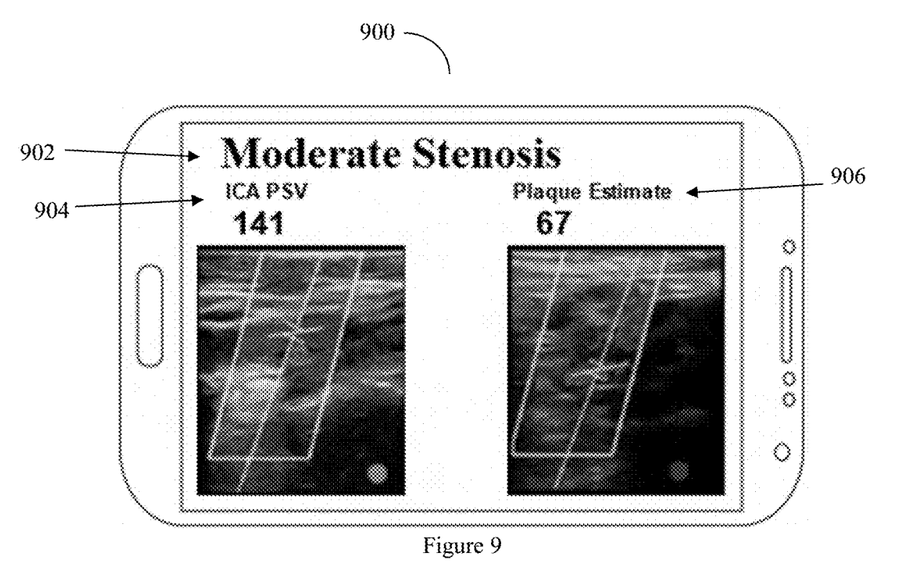

Referring now to FIG. 9, an exemplary embodiment 900 for a medical condition of moderate stenosis 902 is illustrated, in accordance with an embodiment of the present subject matter. To illustrate further, consider a 3D carotid ultrasound as depicting the ICA PSV 904 as 141 and Plaque estimate 906 as 67. In one example, the value of ICA PSV up to 125 may be considered normal to mildly risky. However, with the ICA PSV 904 value of 141, the system 102 may indicate the medical condition of Moderate Stenosis.

Figure 10:
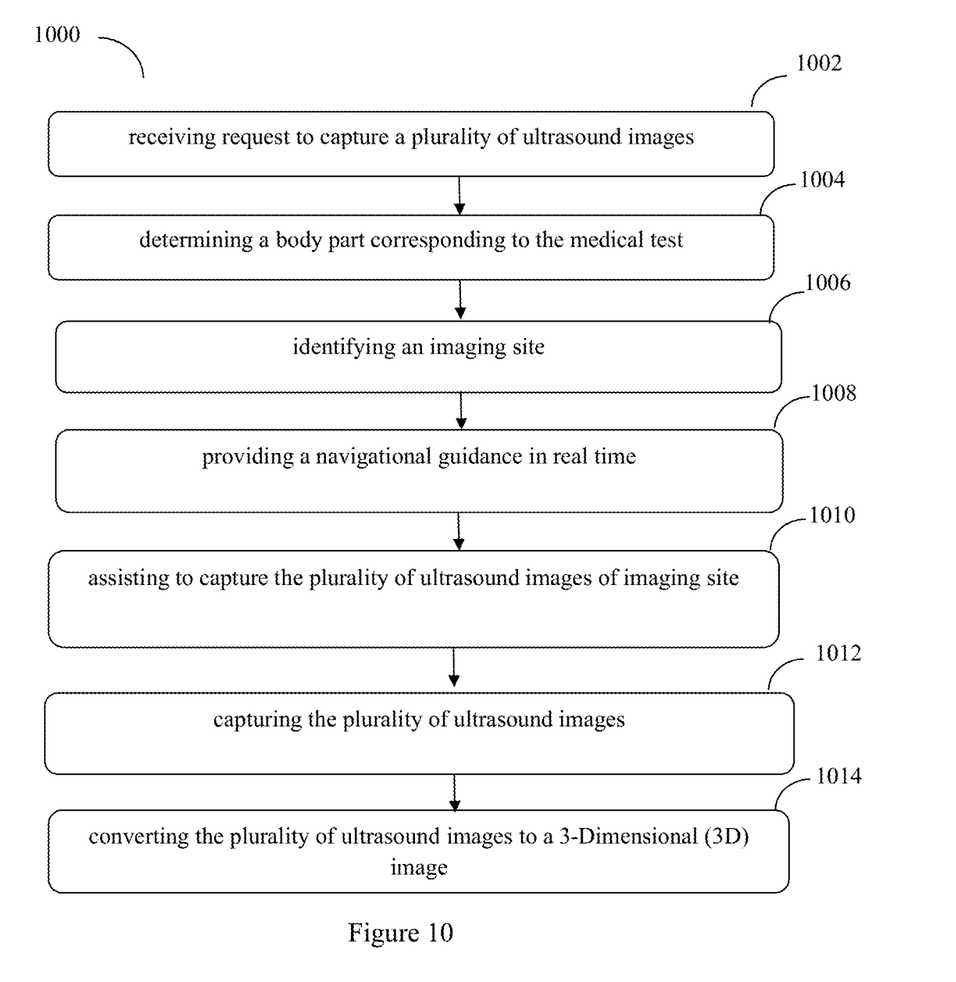
FIG. 10 illustrates a method for acquiring a 3D ultrasound image, in accordance with an embodiment of the present subject matter.

Referring now to FIG. 10, a method 1000 for acquiring a 3D ultrasound image is shown, in accordance with an embodiment of the present subject matter. The method 1000 may be described in the general context of computer executable instructions. Generally, computer executable instructions can include routines, programs, objects, components, data structures, procedures, modules, functions, etc., that perform particular functions or implement particular abstract data types.

The order in which the method 1000 is described is not intended to be construed as a limitation, and any number of the described method blocks can be combined in any order to implement the method 1000 or alternate methods for acquiring a 3D ultrasound image. Additionally, individual blocks may be deleted from the method 1000 without departing from the scope of the subject matter described herein. Furthermore, the method 1000 for creating acquiring a 3D ultrasound image can be implemented in any suitable hardware, software, firmware, or combination thereof. However, for ease of explanation, in the embodiments described below the method 1000 may be considered to be implemented in the above-described system 102.

At block 1002, a request to capture a plurality of ultrasound images for a medical test corresponding to a medical condition may be received. It may be understood that the request may be received from a user on a wireless display device. In one aspect, the request and the medical test corresponding to the medical condition may be stored in the memory 112.

At block 1004, a body part corresponding to the medical test may be determined. It may be noted that the body part may be determined based upon a historical knowledge base in order to capture the plurality of ultrasound images relevant for the medical test. In one aspect, the historical knowledge base may be stored in the memory 112.

At block 1006, an imaging site particular to the medical test may be identified. It may be noted that the imaging site may be identified from the historical knowledge base of the medical test and the imaging site may be a portion of the body part. In one aspect, the imaging site and the historical knowledge base of the medical test and the imaging site may be stored in the memory 112.

At block 1008, a navigational guidance in real time for positioning a handheld ultrasound device at the imaging site may be provided. It may be noted that the navigational guidance may be based on deep learning and the navigational guidance may be provided in natural language. In one aspect, the navigational guidance and the deep learning may be stored in the memory 112.

At block 1010, the user may be assisted to capture the plurality of ultrasound images of the imaging site in real time using deep learning. It may be understood that the assistance may comprise a real time feedback on at least an image quality, automated measurements, coverage calculations, angular calculations, and characterizations specific to the ultrasound images of the medical condition. In one aspect, the assistance and the real time feedback may be stored in the memory 112.

At block 1012, the plurality of ultrasound images of the imaging site may be captured when the handheld ultrasound device may be positioned within a permissible radius of operation. It may be understood that the plurality of ultrasound images may be captured based on the assistance and the plurality of ultrasound images may be a 2-Dimensional (2D) image. In one aspect, the plurality of ultrasound images may be stored in the memory 112.

At block 1014, the plurality of ultrasound images may be converted to a 3-Dimensional (3D) ultrasound image in real time. It may be noted that the plurality of ultrasound images may be stitched together to form the 3D ultrasound image using an Artificial Intelligence (AI) enabled image model. In one aspect, the 3D ultrasound image may be stored in the memory 112.

Exemplary embodiments discussed above may provide certain advantages. Though not required to practice aspects of the disclosure, these advantages may include those provided by the following features.

Some embodiments of the system and the method provide an artificially intelligent approach to perform ultrasound for users, medical professionals other than doctors, radiologists, etc.

Some embodiments of the system and the method may reduce human skill and human time involved in acquiring and interpreting ultrasound images.

Some embodiments of the system and method facilitate early detection of carotid stenosis, lung disease and coronary heart disease.

Some embodiments of the system and method provide fully automated doppler measurements, intima media thickness measurements, plaque detections and risk scoring.

Some embodiments of the system and method provide risk assessment for critical medical emergencies such as stroke and also help in post stroke monitoring, Although implementations for methods and system for acquiring a 3D ultrasound image have been described in language specific to structural features and/or methods, it is to be understood that the appended claims are not necessarily limited to the specific features or methods described. Rather, the specific features and methods are disclosed as examples of implementations for acquiring a 3D ultrasound image.

We claim:

1. A method for acquiring a 3D ultrasound image, the method comprising:
   receiving, by a processor, a request to capture a plurality of ultrasound images for a medical test corresponding to a medical condition, wherein the request is received from a user on a wireless display device;
   determining, by the processor, a body part corresponding to the medical test, wherein the body part is determined based upon a historical knowledge base in order to capture the plurality of ultrasound images relevant for the medical test;
   identifying, by the processor, an imaging site for the medical test, wherein the imaging site is identified from the historical knowledge base of the medical test, and wherein the imaging site is a portion of the body part;
   providing, by the processor, a navigational guidance in real time for positioning a handheld ultrasound device at the imaging site, wherein the navigational guidance is based on deep learning, and wherein the navigational guidance is provided in natural language;
   assisting, by the processor, to capture the plurality of ultrasound images of the imaging site in real time using deep learning, wherein the assistance comprises a real time feedback on at least an image quality, automated measurements, coverage calculations, angular calculations, and characterizations specific to the ultrasound images of the medical condition;
   capturing, by the processor, the plurality of ultrasound images of the imaging site when the handheld ultrasound device is positioned within a permissible radius of operation, and wherein the plurality of ultrasound images is captured based on the assistance, wherein the plurality of ultrasound images is a 2-Dimensional (2D) image; and
   converting, by the processor, the plurality of ultrasound images to a 3-Dimensional (3D) ultrasound image in real time, wherein the plurality of ultrasound images is stitched together to form the 3D ultrasound image, and wherein the plurality of ultrasound images is stitched using an Artificial Intelligence (AI) enabled image model.

2. The method as claimed in claim 1, further comprising:
   analysing the 3D ultrasound image using the deep learning;
   identifying a plurality of characteristics associated with the imaging site from the 3D ultrasound image in real time, wherein the plurality of characteristics comprises a set of morphological specifications of the imaging site, and wherein the plurality of characteristics is pre-defined for the medical test;
   comparing the plurality of characteristics with a trained data model using the deep learning, wherein the trained data model comprises historical data relating to the medical condition associated with a set of users; and
   generating an analysis report for the plurality of characteristics based on the 3D ultrasound image for the medical test.

3. The method as claimed in claim 1, wherein the imaging site is a carotid artery and the medical test is to detect stenosis, and wherein the plurality of characteristics comprises an intima media thickness, a presence of plaque, a height of plaque, a density of plaque, a doppler assessment, and an area of plaque in the carotid artery.

4. The method as claimed in claim 1, further comprises providing the navigational guidance and the assistance in a Virtual Reality (VR) based 3-Dimensional model to the user.

5. The method as claimed in claim 1, further comprises providing the navigational guidance and the assistance in an Augmented Reality (AR) based 3-Dimensional model to the user.

6. The method as claimed in claim 1, further comprises displaying the navigational guidance, the assistance, the plurality of ultrasound image, and the 3-D ultrasound image on a wireless display device in real time.

7. A system for acquiring a 3-D ultrasound image, the system comprising:
a memory;
a processor coupled to the memory, wherein the processor is configured to execute a set of instructions stored in the memory to:
receive a request to capture a plurality of ultrasound image for a medical test corresponding to a medical condition, wherein the request is received from a user on a wireless display device;
determine a body part corresponding to the medical test, wherein the body part is determined to capture the plurality of ultrasound image relevant for the medical test;
identify an imaging site for the medical test, wherein the imaging site is identified from a historical knowledge base of the medical test, and wherein the imaging site is a predefined area of the body part related to the medical test;
provide a navigational guidance to the user in real time for positioning a handheld ultrasound device at the imaging site, wherein the navigational guidance is generated upon identifying the imaging site, and wherein the navigational guidance is based on deep learning, and wherein the navigational guidance is provided in natural language;
assist the user to capture the plurality of ultrasound image of the imaging site in real time using deep learning, wherein the assistance comprises a real time feedback on at least an image quality, automated measurements, coverage calculations, and characterizations specific to the medical condition;
capture the plurality of ultrasound image of the imaging site when the handheld ultrasound device is positioned within a permissible radius of operation, and wherein plurality of ultrasound image is captured based on the assistance, wherein the plurality of ultrasound image is a 2-Dimensional (2D) image; and
convert the plurality of ultrasound image to a 3-Dimensional (3D) ultrasound image in real time, wherein the plurality of ultrasound image is stitched together to form the 3D ultrasound image, and wherein the plurality of ultrasound images are stitched using an Artificial Intelligence (AI) enabled image model.

8. The system as claimed in claim 7, further configured to:
analyse the 3D ultrasound image using the deep learning;
identify a plurality of characteristics associated with the imaging site from the 3D ultrasound image in real time, wherein the plurality of characteristics comprises a set of morphological specifications of the imaging site, and wherein the plurality of characteristics is pre-defined for the medical test;
compare the plurality of characteristics with a trained data model using the deep learning, wherein the trained data model comprises historical data relating to the medical condition associated with a set of users; and
generate an analysis report for the plurality of characteristics based on the 3D ultrasound image for the medical test.

9. The system as claimed in claim 7, wherein the imaging site is a carotid artery and the medical test is to detect stenosis, and wherein the plurality of characteristics comprises an intima media thickness, a presence of plaque, a height of plaque, a density of plaque, a doppler assessment, and an area of plaque in the carotid artery.

10. The system as claimed in claim 7, further configured to provide the navigational guidance and the assistance in a Virtual Reality (VR) based 3-Dimensional model to the user.

11. The system as claimed in claim 7, further configured to provide the navigational guidance and the assistance in an Augmented Reality (AR) based 3-Dimensional model to the user.

12. The system as claimed in claim 7, further configured to display the navigational guidance, the assistance, the plurality of ultrasound image, and the 3-D ultrasound image on a wireless display device in real time.

13. A non-transitory computer program product having embodied thereon a computer program for acquiring a 3D ultrasound image, the computer program product storing instructions, the instructions for:
receiving a request to capture a plurality of ultrasound image for a medical test corresponding to a medical condition, wherein the request is received from a user on a wireless display device;
determining a body part corresponding to the medical test, wherein the body part is determined to capture the plurality of ultrasound image relevant for the medical test;
identifying an imaging site for the medical test, wherein the imaging site is identified from a historical knowledge base of the medical test, and wherein the imaging site is a predefined area of the body part related to the medical test;
providing a navigational guidance to the user in real time for positioning a handheld ultrasound device at the imaging site, wherein the navigational guidance is generated upon identifying the imaging site, and wherein the navigational guidance is based on deep learning, and wherein the navigational guidance is provided in natural language;
assisting the user to capture the plurality of ultrasound image of the imaging site in real time using deep learning, wherein the assistance comprises a real time feedback on at least an image quality, automated measurements, coverage calculations, and characterizations specific to the medical condition;
capturing the plurality of ultrasound images of the imaging site when the handheld ultrasound device is positioned within a permissible radius of operation, and wherein plurality of ultrasound images is captured based on the assistance, wherein the plurality of ultrasound images is a 2-Dimensional (2D) image; and
converting the plurality of ultrasound image to a 3-Dimensional (3D) ultrasound image in real time, wherein the plurality of ultrasound images is stitched together to form the 3D ultrasound image, and wherein the plurality of ultrasound images is stitched using an Artificial Intelligence (AI) enabled image model.

\* \* \* \* \*